United States Patent [19]

Griss

[11] Patent Number: 4,828,566
[45] Date of Patent: May 9, 1989

[54] HIP JOINT IMPLANT

[75] Inventor: Peter Griss, Marburg, Fed. Rep. of Germany

[73] Assignee: Sulzer Brothers Limited, Winterthur, Switzerland

[21] Appl. No.: 11,064

[22] Filed: Feb. 4, 1987

[30] Foreign Application Priority Data

Feb. 18, 1986 [CH] Switzerland .................. 650/86

[51] Int. Cl.$^4$ .................. A61F 2/32; A61F 2/30
[52] U.S. Cl. .................. 623/23; 623/18
[58] Field of Search .................. 623/16, 17, 18, 19, 623/20, 21, 22, 23

[56] References Cited

U.S. PATENT DOCUMENTS

| 4,536,894 | 8/1985 | Galante et al. | 623/22 |
| 4,589,883 | 5/1986 | Kenna | 623/22 |
| 4,636,219 | 1/1987 | Pratt et al. | 623/22 |

FOREIGN PATENT DOCUMENTS

| 0149527 | 7/1985 | European Pat. Off. | 623/23 |
| 2142830 | 1/1985 | United Kingdom | 623/23 |

Primary Examiner—Richard J. Apley
Assistant Examiner—David J. Isabella
Attorney, Agent, or Firm—Kenyon & Kenyon

[57] ABSTRACT

The shank is provided with a recess in the proximal medial region and a U-shaped wire mesh structure is secured within the recess. The wire mesh structure provides for an ingrowth of bone tissue at the medial narrow side of the shank and an absorption of shear micro movements between a bone and the implant. The mesh structure can be secured in place by rivets or by weld seams.

4 Claims, 1 Drawing Sheet

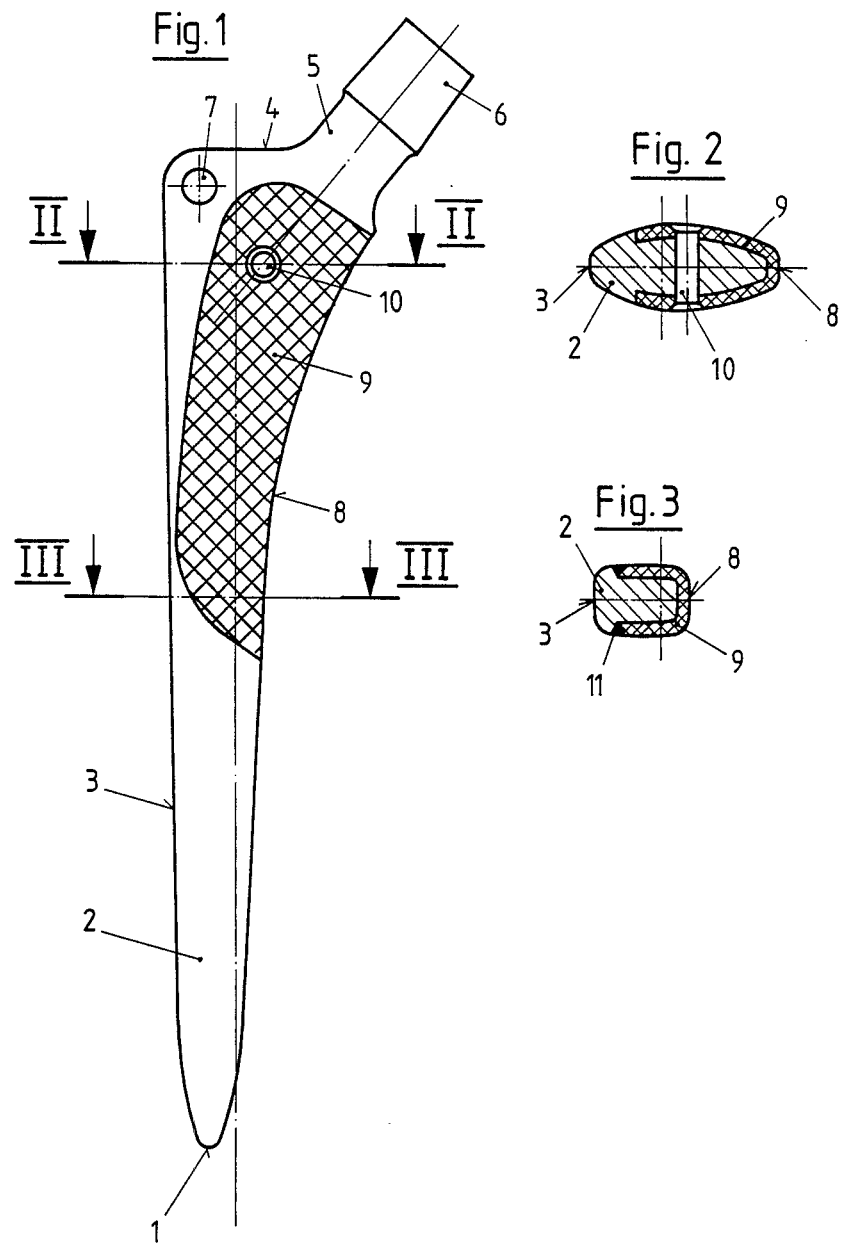

HIP JOINT IMPLANT

This invention relates to a hip joint implant.

As is known, various types of hip joint implants have been constructed with shanks of various shapes and constructions in order to provide a firm anchoring of the implant in a bone. In more recent times, the shanks have been constructed for a cement-free anchorage. For example, German O.S. No. 3505997 describes a hip joint implant with a shank of blade-like construction which widens conically from a distal end toward a proximal end and which has a lenticular disk form in the proximal region. In addition, the shank is provided, at least in the proximal region, with a surface structure on the anterior and posterior blade sides which permits an ingrowth of bone tissue in order to enhance a cement-free anchoring. However, because of the forces which result, particularly through the continual stressing and relief due to bending moments exerted by the joint head of a prosthesis, small thrust movements, i.e. so-called micro movements, occur at the boundary between the cortical tissue of the calcar arc and the medial narrow side of the shank. These micro movements are undesirable as the movements impede accretion of tissue in the region of the pressure-stressed medial narrow side of the shank.

Accordingly, it is an object of the invention to prevent the occurrence of shear movements between a bone and the tank of a hip joint implant.

It is another object of the invention to improve the cement-free anchorage of a hip joint implant in a bone.

It is another object of the invention to be able to absorb micro movements between a bone and an implanted prosthesis shank in an efficient manner.

Briefly, the invention provides a hip joint implant which is comprised of a shank having a blade-like portion extending from a distal end toward a proximal end with a lenticular disk shaped cross-section in a proximal medial region and a wire mesh structure which is secured to the proximal medial region of the blade-like portion and about a medial narrow side of the blade-like portion.

The wire-mesh structure may be of multi-layer construction as well as of U-shape. In addition, the proximal medial region of the blade-like portion may be recessed so that the wire mesh structure is received in flush relation.

The wire mesh structure provides for an ingrowth of bone tissue so that a union between the bone and the implant occurs in a micro region through a plurality of pores. Where the mesh structure is of multi-layer construction, the "internal" elasticity of the individual layers of the mesh structure relative to each other absorbs at least a part of the small shear micro movements thus keeping the movements away from the interface between the bone and mesh surface.

The shank and wire mesh structure consist preferrably of titanium or a titanium alloy. Further, a suitable means is provided for securing the mesh structure to the shank. For example, the means may be in the form of at least one rivet which passes through the mesh structure and the shank. Alternatively, the means may include a plurality of weld seams along at least a peripheral edge of the wire mesh structure. Any other suitable type of mechanical connection may also be used.

These and other objects and advantages of the invention will become more apparent from the following detailed description taken in conjunction with the accompanying drawings wherein:

FIG. 1 illustrates a side view of a hip joint implant constructed in accordance with the invention;

FIG. 2 illustrates a view taken on line II—II of FIG. 2; and

FIG. 3 illustrates a view taken on line III—III of FIG. 1 with a modified securing means.

Referring to FIG. 1, the hip joint implant includes a shank 2 having a blade-like portion extending in conically winding manner from a distal end 1 toward a proximal end. As illustrated, a lateral narrow side 3 merges at the proximal end into a horizontal shoulder 4 which extends in stepless manner to a prosthesis neck 5. In addition, a conical pin 6 is provided on the neck 5 for receiving a joint head (not shown) at the proximal end. A bore 7 is also provided in the transitional region between the narrow lateral side 3 and the horizontal shoulder 4 for the engagement of a guiding and extracting instrument (not shown).

The shank 2 has a medial narrow side 8 which extends on an arc to a medial point of merger with the prosthesis neck 5 as indicated in FIG. 2, the blade-like portion of the shank has a lenticular disk shaped cross-section in the proximal medial region. In addition, the proximal medial region is recessed and receives a wire mesh structure 9 therein in flush relation. This wire mesh structure 9 is of U-shape and is secured to the proximal medial region about the medial narrow side 8 of the blade-like portion.

Referring to FIGS. 1 and 2, a means in the form of a rivet 10 is provided for securing the mesh structure 9 to the shank 2. This rivet 10 passes through the sides of the mesh structure 9 as well as through the shank 2.

The wire mesh structure may be of single layer or of multi-layer construction. In the latter case, the mesh width or pore sizes in the individual layers may be different, for example, decreasing from the outside layer inwardly towards the shank.

Referring to FIG. 3, the means for securing the wire mesh structure 9 to the shank 2 may include a plurality of weld seams 11 along at least at a peripheral edge of the wire mesh structure 9.

The wire mesh structure 9 ensures a firm connection between the implant and a bone, particularly in the region of a calcar arc of the bone, by an ingrowth of bone tissue at the medial narrow side 8. Thus, relative shear movements in the micro range are prevented at the boundary between the shank and bone. Further, the flow of force from the shank to the bone, especially in the heavily pressure loaded region of the calcar arc is improved.

After there has been some ingrowth of bone tissue into the wire mesh structure 9, the shear micro movements between the bone and the implant are absorbed within the wire mesh structure. In this regard, where the mesh structure is formed of several layers, the internal elasticity of the individual layers relative to each other absorbs these micro movements.

What is claimed is:

1. A hip joint implant comprising
   a shank having a blade-like portion extending in conically widening manner form a distal end toward a proximal end with a lenticular disk shaped cross-section in a proximal medial region, a neck extending from said blade-like portion at said proximal end and a pin for receiving a joint head at said proximal end;

a U-shaped wire mesh structure secured to said proximal medial region of said blade-like portion and about a medical narrow side of said blade-like portion; and at least one rivet passing through said mesh structure and said shank for securing said mesh structure to said shank.

2. A hip joint implant as set forth in claim 1 wherein said wire mesh structure is of multi-layer construction.

3. A hip joint implant as set forth in claim 1 wherein siad means includes a plurality of weld seams along at least a peripheral edge of said wire mesh structure.

4. A hip joint implant as set forth in claim 1 wherein said blade-like poriton is recessed in said proximal medial region and receives said wire mesh structure therein in flush relation.

* * * * *

UNITED STATES PATENT AND TRADEMARK OFFICE
CERTIFICATE OF CORRECTION

PATENT NO. : 4,828,566

DATED : May 9, 1989

INVENTOR(S) : Peter Griss

It is certified that error appears in the above-identified patent and that said Letters Patent is hereby corrected as shown below:

Column 1, line 30, "tank" should read --shank--.
Column 2, line 42, "at least at a" should read --at least a--.
Column 2, line 63, "form should read --from--.
Column 3, line 3, "medical" should read --medial--.
Column 4, line 7, "poriton" should read --portion--.

Signed and Sealed this

Thirteenth Day of March, 1990

Attest:

JEFFREY M. SAMUELS

*Attesting Officer*   *Acting Commissioner of Patents and Trademarks*